United States Patent
Berndt et al.

(10) Patent No.: US 11,506,647 B2
(45) Date of Patent: Nov. 22, 2022

(54) METHOD FOR OPERATING A GAS CONCENTRATION MONITORING SYSTEM, GAS-MEASURING DEVICE, CENTRAL UNIT, GAS CONCENTRATION MONITORING SYSTEM AS WELL AS COMPUTER PROGRAM PRODUCT

(71) Applicant: Dräger Safety AG & Co. KGaA, Lübeck (DE)

(72) Inventors: Malte Berndt, Lübeck (DE); Ingo Kaneblei, Lübeck (DE); Ulf Ostermann, Rümpel (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 647 days.

(21) Appl. No.: 16/448,604

(22) Filed: Jun. 21, 2019

(65) Prior Publication Data
US 2020/0400636 A1 Dec. 24, 2020

Related U.S. Application Data

(63) Continuation of application No. 14/360,839, filed as application No. PCT/EP2012/073844 on Nov. 28, 2012, now Pat. No. 10,371,682.

(30) Foreign Application Priority Data

Nov. 28, 2011 (DE) ...................... 10 2011 119 570.3

(51) Int. Cl.
*G01N 33/00* (2006.01)

(52) U.S. Cl.
CPC ..... *G01N 33/0073* (2013.01); *G01N 33/0006* (2013.01); *G01N 33/0065* (2013.01); *G08C 2200/00* (2013.01)

(58) Field of Classification Search
CPC .......... G01N 33/0073; G01N 33/0006; G01N 33/0065; G08C 2200/00
See application file for complete search history.

(56) References Cited

U.S. PATENT DOCUMENTS 5,908,600 A * 6/1999 Simi .................. G01N 33/0031
324/71.5
6,442,639 B1 8/2002 McElhattan et al.

FOREIGN PATENT DOCUMENTS

DE 102004024809 A1 12/2005

* cited by examiner

*Primary Examiner* — Manuel A Rivera Vargas
(74) *Attorney, Agent, or Firm* — McGlew and Tuttle, P.C.

(57) ABSTRACT

A method is provided for operating a gas concentration monitoring system as well as a gas-measuring device, a central unit, a gas concentration monitoring system as well as computer program product. The safety of persons or the safety of a situation is determined with respect to at least one hazardous gas. The concentration of the gas is provided to a memory and analysis device. A measured value rating number is determined for a preset period of use. A number of instances, of the measured concentration values exceeding of a preset gas concentration limit value is input. A safety code is determined from at least one of: the measured concentration values, the measured value rating numbers and from the a total number of instances in which a gas concentration limit value was exceeded.

29 Claims, 3 Drawing Sheets

METHOD FOR OPERATING A GAS CONCENTRATION MONITORING SYSTEM, GAS-MEASURING DEVICE, CENTRAL UNIT, GAS CONCENTRATION MONITORING SYSTEM AS WELL AS COMPUTER PROGRAM PRODUCT

CROSS REFERENCE TO RELATED APPLICATIONS

This application is a continuation of, and claims the benefit of priority under 35 U.S.C. § 120 of U.S. application Ser. No. 14/360,839 filed May 27, 2014, which is a United States National Phase Application of International Application PCT/EP2012/073844 filed Nov. 28, 2012 and claims the benefit of priority under 35 U.S.C. § 119 of German Patent Application DE 10 2011 119 570.3 filed Nov. 28, 2011, the entire contents of which are incorporated herein by reference.

FIELD OF THE INVENTION

The present invention pertains to a method for operating a gas concentration monitoring system for detecting the gas concentration of at least one gaseous substance, in which a safety code for assessing the safety situation in a predetermined operating area is determined. The present invention pertains, furthermore, to a gas-measuring device as well as to a computer program product for carrying out the method according to the present invention.

BACKGROUND OF THE INVENTION

Gas-measuring devices, especially portable gas-measuring devices, are used to monitor the gas concentration of at least one gaseous substance in a predetermined operating area, e.g., an industrial plant, such as a refinery. The gaseous substances may be, e.g., carbon monoxide, hydrogen sulfide, oxygen or other toxic gaseous substances. These gas-measuring devices have for this one or more sensors in order to measure the gas concentration of the gaseous substance in question in the ppm range. Such gas-measuring devices usually have two limit values, which trigger an alarm. These are a low limit value, where a pre-alarm (also called A1) is triggered when this is exceeded, and a high limit value, where a master alarm (also called A2) is triggered when this is exceeded. The gas-measuring device generates an acoustic and/or optical alarm in order to warn the user of the gas-measuring devices in response to the exceeding of a limit value, for example, a workplace limit value (WLV) or a lower explosion limit (LEL), which sets the maximum allowable concentration of a gaseous substance. To guarantee reliable operation of the gas-measuring devices, it is necessary for the gas-measuring devices to be checked regularly. For example, so-called bump tests are carried out for this at relatively short intervals and calibrations at relatively long intervals compared to the former. These bump tests and calibrations are carried out with so-called docking stations, which admit for this an inert gas, e.g., nitrogen, or fresh air, and a test gas containing the gaseous substance to be detected to the sensor of a gas-measuring device. However, it is desirable to obtain more information on the safety situation in a predetermined operating area.

SUMMARY OF THE INVENTION

An object of the present invention is therefore to provide a method for obtaining more safety-relevant information for assessing the safety of persons.

The object of the present invention is accomplished by a method for determining the safety of the person from at least one gas threatening the person and especially at least one toxic gas and/or at least one combustible gas and/or oxygen deficiency and/or oxygen excess, said method having the steps of:
  inputting the concentration of each of the at least one gas determined by the plurality of gas-measuring devices into a memory and analysis means;
  determination of a measured value rating number for a preset period of use of the gas-measuring device in question in the memory and analysis means from the measured values for the concentration of each of the at least one gas;
  inputting a number of instances in which a preset gas concentration limit value is exceeded by the measured value for each of the gas-measuring devices into a data; and
  determination of a safety code for rating the safety situation/safety of persons for a plurality of measurement sites as a whole, at which the measurements were performed by the gas-measuring device, from the measured values of the plurality of gas-measuring devices and/or from the measured value rating numbers determined from the measured values of the plurality of gas-measuring devices and from the total number of instances in which a gas concentration limit value is exceeded, which is determined from the measured value of the plurality of gas-measuring devices.

Further, the object of the present invention is accomplished by a method with the steps of:
  inputting measured values for the concentration of each of the at least one gas into a memory and analysis means,
  determination of a measured value rating number derived for a preset period of use of the respective gas-measuring device from the measured values for the concentration of each of the at least one gas in the memory and analysis means, inputting a number of instances in which a preset gas concentration limit value was exceeded by the measured values for each of the gas-measuring device into a memory, and
  determination of a safety code for rating the safety situation/safety of persons for a plurality of measurement sites as whole, at which the measurements performed by the gas-measuring device were carried out, from the measured values of the plurality of gas-measuring devices and/or from the measured value rating numbers determined from the measured values of the plurality of gas-measuring devices and from the total number of instances in which a gas concentration limit value was exceeded, which was determined from the measured values of the plurality of gas-measuring devices.

The methods consequently use data, e.g., in the form of one or more data sets, which were obtained when gas concentration measurements were carried out with a plurality of gas-measuring devices, e.g., during the time during which the one user or the users carried with him/them, e.g., a portable gas-measuring device each in an operating area in order to be warned, if necessary, of excessively high concentrations of a toxic gaseous substance. Data are detected and recorded continuously in the process. As an alternative, a data set can then be generated, e.g., by a gas-measuring device when the gas-measuring device has detected a gas concentration that is above a permissible limit value, e.g., the workplace limit value (WLV) or a lower explosion limit (LEL). Besides the exceeding of the limit value, the data set may contain more information, e.g., the type of the gaseous substance, if, e.g., a plurality of different gaseous substances can be detected with the gas-measuring device, the extent to which the limit value is exceeded, the duration for which the limit value is exceeded, as well as a dose, which is determined from the extent and the duration to which and for which the limit value was exceeded.

The data are then transmitted from each gas-measuring device to the memory and analysis means. The transmission of the data may take place, e.g., by a data storage medium, e.g., a USB stick, on which the data are first transmitted from the gas-measuring device, and they are then transmitted from the USB stick into the memory and analysis means. As an alternative, transmission of the data may take place via electric contacts of the gas-measuring device, in which case, e.g., a docking station for performing bump tests or calibrations have corresponding mating contacts in order to form an electrically conductive connection for transmitting the data. The docking station itself may, in this case, have a data bank, or the docking station is connected with the data bank, e.g., via a computer network. Finally, the transmission of the data set may also take place in a wireless manner, so that it is not necessary to establish an electric contact.

A safety code, which contains information on how often a limit value was exceeded and/or how conscientiously (frequently) the gas-measuring devices were checked, so that their reliable operability is guaranteed, on the basis of the information contained in the data on exceeding of the limit value and/or on checks of the gas-measuring devices that were not performed, is then determined from the data. The safety code thus makes it possible to assess the safety situation in an operating area, e.g., an industrial plant, such as a refinery, because leakage of gas from the industrial plant is also detected by detecting instances in which a limit value was exceeded.

The safety code may, furthermore, be observed over a rather long period of time in order to recognize changes in the safety situation. In addition, the safety code can be compared with safety codes of other areas of a plant or also of plants among each other in order to thus obtain additional information.

The safety code is a single number that expresses the safety situation as a summary of a plurality of factors in the form of a sum parameter. Different colors may also be assigned to different value ranges of the safety code, e.g., green to a quite safe safety situation, yellow to a precarious safety situation, which requires increased attention, and red to a safety situation that requires immediate action.

Provisions are preferably made for the measured value rating number derived for a preset period of use of the respective gas-measuring device to be an average determined for the preset period of use. The definition of the period of use also covers the interval between uses of a gas-measuring device. A use interval is the period from the time the gas-measuring device is put into operation by a user, e.g., at the beginning of a shift, until the end of use by the user, e.g., at the end of the shift. Other variables may also be used as the basis for the measured value rating number instead of the average.

Provisions are preferably made for always determining the safety code by weighted addition of the measured values and/or the measured value rating number for the preset period of use of the respective gas-measuring device, with a derived measured value rating number and a measured value rating number determined from a number of instances in which a gas concentration limit value was exceeded by the measured values together with an identification code of the respective gas-measuring device.

Weighting of the events can be performed by a weighted addition, so that, e.g., the events exceeding the limit value are taken into account with a greater weight than is the measured value rating number.

Weighted addition leads to an intuitively easy-to-understand safety code, in which the number zero is a very good value and the scale of the safety code is upwardly open, i.e., it may assume high numbers as desired. Thus, it is not suggested that there is a 100% risk, unlike in the case of data expressed in percentage, which can assume a value from zero to 100%.

Further, provisions are preferably made for the method to additionally have the following step: Inputting of the duration of the detected exceeding of the gas concentration limit value preset period of use of the respective gas-measuring device. This is input into a memory and analysis means from each of the gas-measuring devices, and provisions are preferably made for the determination of the safety code to be performed such that the duration of the detected exceeding of the gas concentration limit value is taken functionally into account and especially by weighted addition of the duration.

The duration of the detected exceeding of the gas concentration limit value within the use interval of the gas-measuring device is defined as the average duration of the alarm, e.g., the duration of a pre-alarm (A1) or of a master alarm (A2) of the gas-measuring device or per gas-measuring device in case of a plurality of gas-measuring devices in minutes, i.e., the total alarm duration of all gas-measuring devices of a fleet (group) of gas-measuring devices, divided by the number of gas-measuring devices and standardized for the number of minutes of alarm per use interval, e.g., one day. The duration of one or more exceeding of the limit value event is determined, doing so relative to a use interval of the gas-measuring device.

Further, provisions are preferably made for the step of determining the safety code to comprise:
  determination of the number of checks performed on each gas-measuring device in a checking interval, especially of the calibrations and/or bump tests;
  comparison of the number with the checks determined in a checking interval, especially of the calibrations and/or bump tests, with a desired value of the number of checks in a use interval, and
  taking the difference between the number of checks determined and the desired value into account in the determination of the safety code.

The checks not performed are determined by comparing the number of checks performed with the desired value. Skipped checks are detected, and they are detected relative to a use interval of the gas-measuring device. Calibrations are identified here as complete checks including the determination of all calibration parameters, while a bump test is defined as a kind of rapid test, in which a function test is performed by exposing the sensor to a test gas without determination of calibration parameters.

Provisions are preferably made for the step of taking into account the difference to include the differently weighted addition of the number of skipped calibrations and bump tests. This can be performed by using weighting factors, a first weighting factor to the skipped calibrations and a second weighting factor to the bump tests. For example, the second weighting factor may be greater than the first weighting factor. The second weighting factor may thus be 1.5 to 3 times greater than the first weighting factor. For example, the second weighting factor may be twice the first weighting factor in order to have skipped bump tests be reflected especially strongly in the safety code. Further, provisions are preferably made for the step of determining the safety code to include the differently weighted addition of the number of skipped calibrations and bump tests. This can be performed by using weighting factors, wherein a first weighting factor is assigned to the skipped calibrations and a second weighting factor is assigned to the bump tests. For example, the second weighting factor may be greater than the first weighting factor. Thus, the second weighting factor may be 1.5 to 3 times greater than the first weighting factor. For example, the second weighting factor may be twice the first weighting factor in order to have skipped bump tests be reflected especially strongly in the safety code.

To achieve a further refinement of the validity of the safety code, provisions are preferably made for the step of determining the safety code to include the weighting of the number of skipped calibrations with a first weighting factor, the weighting of the number of skipped bump tests with a second weighting factor, and the weighting of the duration of the detected exceeding of the gas concentration limit value with a third weighting factor. The third weighting factor may be 2 to 5 times greater than the first weighting factor. For example, the third weighting factor may be 3 times the first weighting factor and 1.5 times greater than the second weighting factor, so that especially critical limit value exceedings affect the safety code especially strongly. Further, informative information can be obtained if filtering of the data with respect to the model of the gas-measuring device and/or the field of use of the gas-measuring device and/or the users of the gas-measuring device and/or the user groups of the gas-measuring device and/or the period of use of the gas-measuring device is performed for determining the safety code. It is thus possible to determine safety codes that are related to a certain model of gas-measuring device of a fleet with different device models and thus make it possible to compare different device models. Further, safety codes can be determined that are related to the field of use of the gas-measuring device, i.e., e.g., to a certain area of industrial premises, so that special safety situations can be assigned to certain geographic areas. In addition, user-related or user group-related safety codes can be determined, so that it can be determined whether the safety situation of certain users or user groups differs significantly from that of other users or user groups.

To obtain data unambiguously assigned to a use interval, provisions are preferably made for a reset signal to be generated, upon the receipt of which the gas-measuring device generates new data after transmission of the exiting data. The reset signal is generated for this when, e.g., a user puts down the gas-measuring device. The memory of the gas-measuring device is then deleted and new data can be generated when the gas-measuring device is put into operation again.

Further, provisions are preferably made for the data to contain at least:
- a gas-measuring device identification number of the gas-measuring device and/or
- a gas-measuring device model number of the gas-measuring device and/or gas-measuring device measured data detected with the gas sensor within a use interval of the gas-measuring device and/or
- an operating time, especially duration of a use interval, of the gas-measuring device, and/or
- acceleration values detected with an acceleration sensor within a use interval of the gas-measuring device and/or a user identification number for identifying a user of the gas-measuring device.

The respective data can be assigned to the respective gas-measuring devices with a gas-measuring device identification number of the gas-measuring device. By logging which user is taking which gas-measuring device of a fleet of gas-measuring devices with him, this makes it possible to perform an especially simple user- or user group-related analysis of the safety codes.

Simple assignment of data to devices of the same model of a fleet of devices and thus a device-specific analysis of safety codes is possible with a gas-measuring device model number.

The gas concentration measured data detected with the gas sensor within a use interval of the gas-measuring device make it possible to assess whether, e.g., an exceeding of the limit value occurred abruptly or whether it developed only gradually, which can give indications as to the cause of the exceeding of the limit value.

The operating time of the use of the gas-measuring device can be taken into account in the assessment of the safety code by the operating time, especially the use interval duration. Thus, the probability of malfunctions of the gas-measuring device increases with increasing operating time, e.g., in case of the depletion of batteries, which are used to supply the gas-measuring device with energy.

It can be assessed with the acceleration values whether the gas-measuring device was subject to acceleration values during a use interval that could lead to mechanical damage to the gas-measuring device or components thereof.

Finally, a user identification numbers simplifies the identification of a user of the gas-measuring device and optionally the assignment of a user to a user group and thus makes possible a person-specific assessment of the safety situation, which can possibly be improved by specific training.

Further, a gas-measuring device as part of a gas concentration monitoring system belongs to the object of the present invention. The gas-measuring device has a gas sensor for measuring the gas concentration of at least one gaseous substance.

In addition, the gas-measuring device has a comparison means. The comparison means is designed to compare a measured value detected with the gas sensor in the form of gas concentration measured data with a gas concentration limit value, e.g., a workplace limit value (WLV) or a lower explosion limit (LEL).

The gas-measuring device has, furthermore, a monitoring means. It is detected with the monitoring means whether a prescribed checking of the operability, especially of the calibrations and/or bump test of the gas-measuring device, was performed within a checking interval.

A data set generation module of the gas-measuring device is connected with the comparison means and the monitoring means. The data set generation module generates data when the measured value determined in the form of gas concentration measured data exceeds the gas concentration limit value, and/or when a prescribed checking of the operability, such as calibration and/or a bump test were not performed within a checking interval.

Finally, the gas-measuring device has a gas-measuring device interface for transmitting the data, which is preferably connected for this with the data generation module. As an alternative or in addition, provisions are preferably made for the gas-measuring device to have a memory and analysis unit for analyzing the data, in order to determine a safety code for rating the safety situation in a predetermined operating area by analyzing the data. The memory and analysis unit has a design analogous to that of the analysis module explained below, but the memory and analysis unit is assigned to the gas-measuring device rather than to the memory and analysis means. However, the same advantages and design possibilities are analogously obtained as in the analysis module.

Provisions are preferably made for the memory and analysis unit to be designed to determine the number of checks performed on the gas-measuring device during a checking interval, especially of the calibrations and/or bump tests, for comparing the number of checks determined during a checking interval, especially of the calibrations and/or bump tests, with a desired value for the number of checks during a checking interval, and/or for taking into account the difference between the number of checks determined and the desired value in the determination of the safety code.

Provisions are preferably made for the memory and analysis unit to be designed to take into account the difference of the skipped calibrations and bump tests.

The gas-measuring device preferably has an acceleration sensor for detecting accelerations acting on the gas-measuring device. It can thus be detected whether the gas-measuring device was subjected to accelerations, due to improper use, which could lead to damage to the gas-measuring device or components thereof.

The gas-measuring device is preferably designed to generate new data upon receiving a reset signal. The memory of the gas-measuring device is deleted upon receipt of the reset signal and new data can be generated when the gas-measuring device is put into operation again.

In addition, the data set generation module of the gas-measuring device is preferably designed to degenerate data, which contain at least:
 a gas-measuring device identification number of the gas-measuring device and/or
 a gas-measuring device model number of the gas-measuring device and/or
 gas concentration measured values detected with the gas sensor within a use interval of the gas-measuring device and/or
 an operating time, especially use interval duration, of the gas-measuring device and/or
 acceleration values detected with an acceleration sensor within a use interval of the gas-measuring device and/or
 a user identification number for identifying a user of the gas-measuring device.

This facilitates the analysis of the safety codes, as this was already explained above with reference to the method according to the present invention.

In addition, a memory and analysis means or central unit as part of a gas concentration monitoring system belongs to the object of the present invention.

The memory and analysis means has an input interface. Data that are transmitted from a gas-measuring device to a data bank of the central unit can be input with the input interface. The data themselves were obtained by means of a gas-measuring device, as this was already explained in the description of the method according to the present invention.

The memory and analysis means has a data bank module, which is designed to store and read out data.

In addition, the memory and analysis means has an analysis module, which has access to the data stored by the data bank module. The analysis module is designed to analyze the stored data in order to determine the safety code for rating the safety situation in a predetermined operating area.

Provisions are preferably made for the analysis module to be designed to form the safety code by a weighted addition of at least:
 the number of skipped checks of the operability, especially of the calibrations and/or bump tests, of the gas-measuring device, and
 the duration of the detected exceeding of the gas concentration limit value within the use interval of the gas-measuring device.

As is explained in reference to the method according to the present invention, the duration of the detected exceeding of the gas concentration limit value within the use interval of the gas-measuring device is defined as the average alarm duration, e.g., the duration of a pre-alarm (A1) or of a master alarm (D2) of the gas-measuring device per gas-measuring device in case of a plurality of gas-measuring devices in minutes, i.e., the total alarm duration of all gas-measuring devices of a fleet (group) of gas-measuring devices, divided by the number of gas-measuring devices and standardized for the number of minutes of alarm per day. For example, limit value exceedings can thus be taken into account with a heavier weight than skipped checks. As was also explained already in reference to the method according to the present invention, an intuitively easy-to-understand safety code is obtained by the weighted addition.

Provisions are preferably also made for the analysis module to be designed to weight the number of skipped calibrations and bump tests differently.

As was explained in reference to the method according to the present invention, skipped bump tests can thus be reflected with an especially heavy weight in the safety code.

Further, provisions are preferably made for the analysis module to be designed to weight the number of skipped calibrations with a first weighting factor, the skipped bump tests with a second weighting factor, and the duration of the detected exceeding of the gas concentration limit value with a third weighting factor.

As was explained with reference to the method according to the present invention, for example, especially critical limit value exceedings can affect the safety code especially strongly.

Furthermore, provisions are preferably made for the analysis module to have a filter function, with which the data can be filtered with respect to the model of the gas-measuring device and/or to the field of use of the gas-measuring device and/or to the users of the gas-measuring device and/or to the user groups of the gas-measuring device and/or to the use time of use of the gas-measuring device for determining the safety code.

As was explained in reference to the method according to the present invention, it is thus possible, e.g., to determine safety codes that are related to a certain device model of a fleet of devices with different device models and thus make it possible to compare different device models. Further, safety codes can be determined that are related to the field of use, i.e., a certain area of plant premises, of the gas-measuring device, so that special safety situations can be assigned to certain geographic areas. In addition, user-related or user group-related safety codes can be determined so that it is possible to determine whether the safety situation for certain users or user groups differs significantly from that for other users or user groups.

In addition, the memory and analysis means is preferably designed to generate a reset signal, upon receipt of which a gas-measuring device generates new data (a new data set).

As was explained in reference to the method according to the present invention, it is thus possible to obtain, e.g., data assigned to a use interval.

As was also explained already in reference to the method according to the present invention, data can be stored and read out with the data bank module and analyzed with the analysis module, said data containing at least:
- an identification number of the gas-measuring device and/or
- a model number of the gas-measuring device and/or gas concentration measured data detected with the gas sensor within a use interval of the gas-measuring device and/or
- an operating time, especially use interval duration, of the gas-measuring device and/or
- acceleration values detected with an acceleration sensor within a use interval of the gas-measuring device and/or
- a user identification number for identifying user of the gas-measuring device, which facilitates the analysis of the safety codes, as this was already explained above with reference to the method according to the present invention.

The memory and analysis means may be designed solely to input data of gas-measuring devices, to store them in a data bank and to analyze them in order to determine the safety code. As was described already, the transmission of the data may take place by means of a data storage medium, e.g., a USB stick, on which the data set is first transmitted from the gas-measuring device, and subsequently from the USB stick into the data bank. As an alternative, the memory and analysis means, like the gas-measuring devices, can be designed to transmit the data with wireless transmission, so that it is not necessary to establish an electric contact. For example, the memory and analysis means, like the gas-measuring devices, may be designed such that when the distance between the memory and analysis means and one of the gas-measuring devices drops below a minimum distance, both components establish a wireless connection for data transmission and the data are subsequently transmitted from the gas-measuring device to the memory and analysis means.

Provisions are preferably made for the memory and analysis means to have a device for checking the gas-measuring device for operability, especially for performing calibrations and/or bump tests. Such devices for checking the operability of the gas-measuring device are known and are also called docking stations.

The docking station has a plurality of mounting sites for a gas-measuring device each. When inserted into a mounting site, a bump test or a calibration can be performed with the docking station. An electric connection is formed between the docking station and the gas-measuring device in the mounting site via electric contacts of the docking station. These electric contacts of the docking station and of the gas-measuring device form an interface connection for transmitting the data that are archived in the memory of the gas-measuring device.

One or more of the docking stations are connected with the memory and analysis means, e.g., a main central unit of the gas concentration monitoring system for exchanging data with one another, e.g., by a computer network. A data bank with a computer, which has access to the data bank and analyzes the data in order to determine the safety code, may be assigned to the main central unit.

As an alternative to this, one docking station or each of the docking stations of the gas concentration monitoring system may be additionally assigned to a data bank of its own with a computer, which has access to the data bank of its own, but also to the other data banks, to determine the safety code. Further, one docking station or each of the docking stations may have an output means, e.g., in the form of a display, to display the safety codes determined besides displaying further information.

Finally, a gas concentration monitoring system with a memory and analysis means, according to the present invention, and with a plurality of gas-measuring devices according to the present invention as well as a computer program product, which can be loaded into a computer of a memory, and an analysis means according to the present invention to execute all steps of a method according to the present invention when the computer program product is executed in the computer, belongs to the accomplishment of the object of the present invention.

Further advantageous embodiments of the present invention as well as exemplary embodiments herefor will be explained in more detail below in connection with the drawing figures attached. Functionally similar parts or components are at times designated by the same reference numbers. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
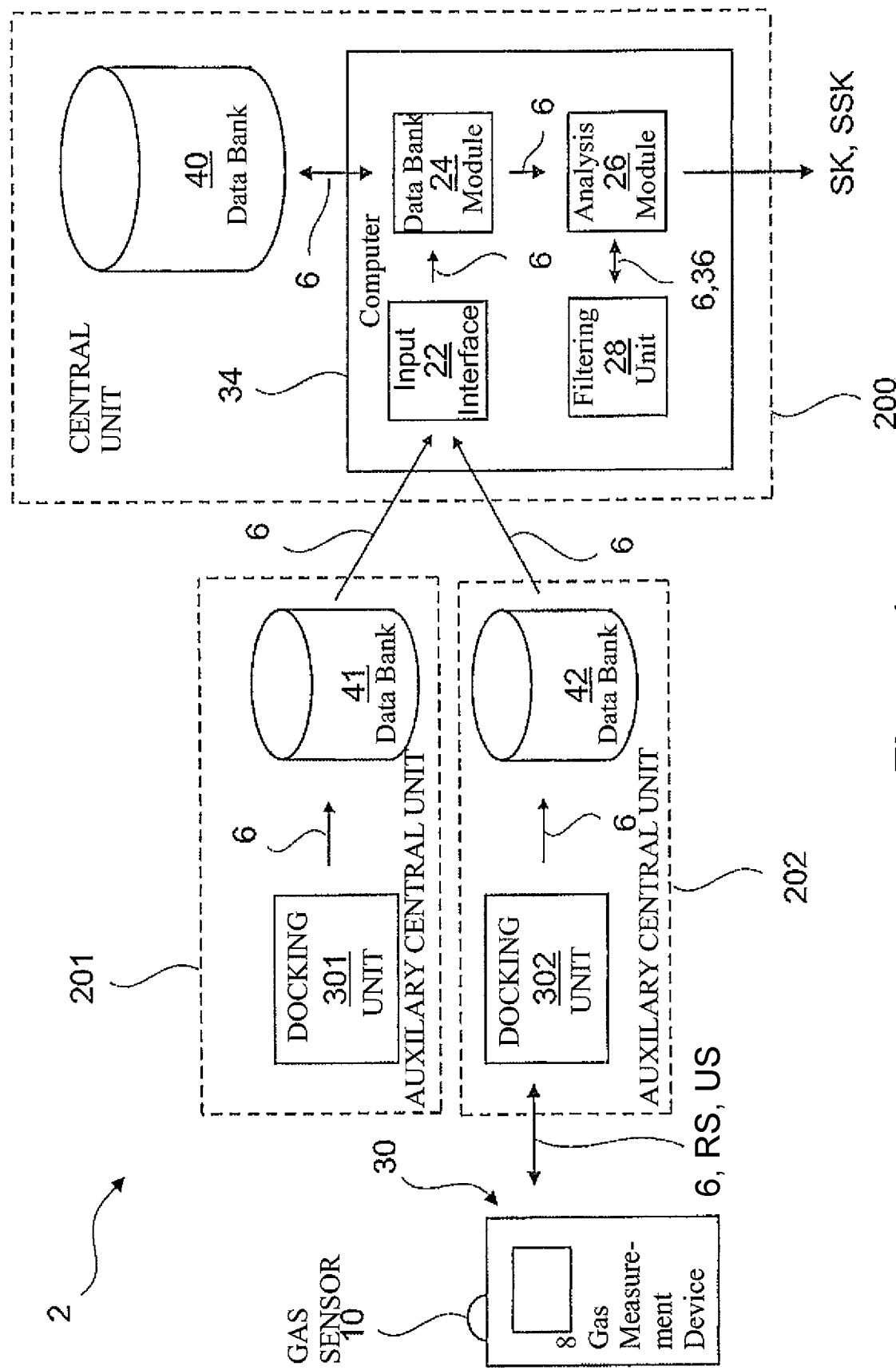
FIG. 1 is a schematic view of the design of an exemplary embodiment of a gas concentration monitoring system according to the present invention.

Reference is first made to FIG. 1.

The gas concentration monitoring system 2 has a fleet (group) of gas-measuring devices with a plurality of gas-measuring devices 8 with a gas sensor 10 each for detecting at least one gaseous substance, of which only one gas-measuring device 8 is shown in FIG. 1 for simplicity's sake. The concentration of carbon monoxide, hydrogen sulfide and oxygen as gaseous substances is detected in the ppm range in this exemplary embodiment. Further, the gas-measuring device 8 is of a portable design in this exemplary embodiment and can be carried along by a user. In this exemplary embodiment, the gas concentration monitoring system 2 has a main central unit 200 and two further auxiliary central units 201, 202, as a memory and analysis means and central units, which have a device each for checking the gas-measuring device for operability and will hereinafter be called docking stations 301, 302 for simplicity's sake. The central unit 200 and the auxiliary central unit 201, 202 are connected with one another in this exemplary embodiment via a computer network for data exchange.

A data bank 40 is assigned to the main central unit 200 and a data bank 41, 42 each is assigned to the auxiliary central units 201, 202. A computer each is assigned to each of the data banks 40, 41, 42, but only the computer 34 assigned to the main central unit 200 is shown in FIG. 1. However, it is obvious that a corresponding computer may be or is likewise assigned to each of the auxiliary central units 201, 202.

The computer 34 of the main central unit 200 has access to the data bank 40, 41, 42 in this exemplary embodiment and can write data in the form of data sets 6 into the respective data bank 40, 41, 42 and read out said data.

To analyze the data sets 6, the computer 34 has an input interface 22, a data bank module 24, an analysis module 26 and a filter function 28, but FIG. 1 shows only the components that are assigned to the central unit 200. These components may be designed as pure hardware components, as pure software components, or as a combination thereof, and they may thus be part of a computer program product.

A data set 6 is input with the input interface 22; this data set 6 was read out from the gas-measuring device 8 and was then stored in the data banks 42 of the two data banks 41, 42 and then transmitted later, e.g., upon a prompt by the main central unit 200, to the data bank 40 of the main central unit 200 and was archived there.

The data bank module 24 of the computer, with which the data set 6 can be read out and stored, is provided for this.

Via the data bank module 24, the analysis module 26 of the computer 34 has access to the data set 6 being stored by the data bank module 24. The analysis module 26 is designed to analyze the data set 8 being stored or a plurality of data sets 8 in order to determine the safety code SK for rating the safety situation in a predetermined operating area.

The data sets 6 can be filtered with the filter function 28 with respect to the model of the gas-measuring device 8 and/or to the field of use of the gas-measuring device 8 and/or to the users of the gas-measuring device 8 and/or to the user groups of the gas-measuring device 8 and/or to the use time of the gas-measuring device 8. The result is a filtered data set 36, which sends the filter function 28 back to the analysis module 26, and which can then be analyzed by the analysis module 26 to determine further, special safety codes SSK, as it will be explained later.

Figure 2:
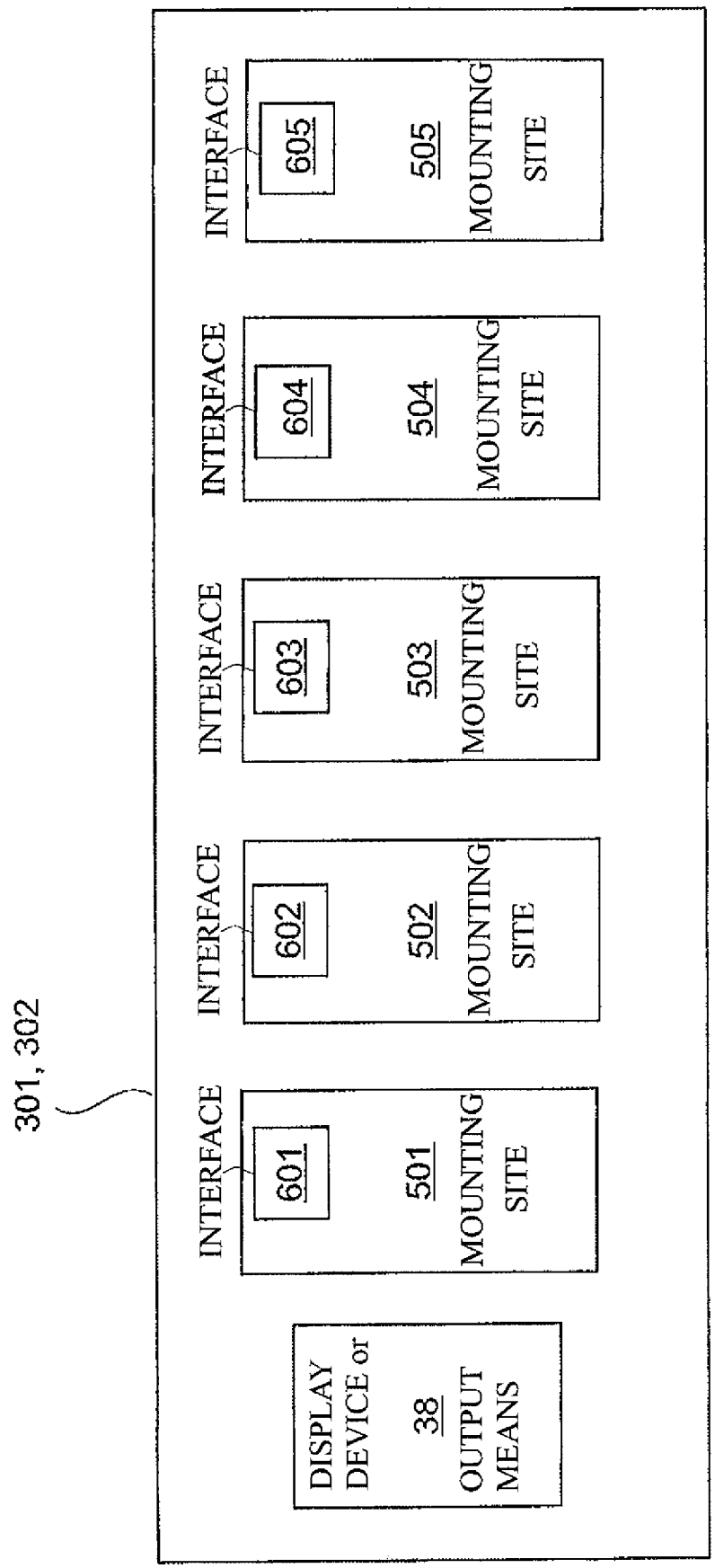
FIG. 2 is a schematic view of the design of an exemplary embodiment of a docking station according to the present invention.

With additional reference to FIG. 2, the design of the auxiliary central units 201, 202 with their docking stations 301, 302 will be explained now. As was mentioned already, the auxiliary central units 201, 202 have a data bank 41, 42 each, to which a computer each is likewise assigned, which has the same design as the computer 34 of the main central unit 34, so that a detailed description of these components can be omitted here, because they are identical.

Contrary to the central unit 200, the auxiliary central units 201, 202 have a docking station 201, 202 each. Each of the docking stations 201, 202 has a plurality of mounting sites 501, 502, 503, 504, 505 for a gas-measuring device 8 each. Inserted into one of the mounting sites 501, 502, 503, 504, 505, a bump test or a calibration can be performed with the docking station 201, 202.

A mounting site interface 601, 602, 603, 604, 605, which is designed to establish an electric contact between the docking station 301, 302 and the gas-measuring device 8, is assigned to each of the mounting sites 501, 502, 503, 504, 505. This makes it possible to transmit a data set 6 from the gas-measuring device 8 to the auxiliary central units 201, 202 to archive the data set 6 in the data bank 41, 42 (see FIG. 1).

Further, one docking station 201, 202 or each of the docking stations 201, 202 may have an output means 38, e.g., in the form of a display, with which it can be displayed whether a bump test or a calibration was successfully concluded, or is just being carried out. In addition, it can be displayed with the display means 38 that a data set 6 was transmitted or is just being transmitted. Finally, the content of the data set 6 can be visualized with the display means 38, and the display means 38 can be used to display the safety code SK. For example, different colors can be assigned to different value ranges of the safety code SK, e.g., green to a quite safe safety situation, yellow to a precarious safety situation, which requires increased attention, and red to a safety situation that requires immediate action.

Finally, the docking stations 301, 302 are designed to generate a reset signal (see FIG. 1), with which—as will be described later—a deletion operation is triggered after conclusion of a reading-out operation of a data set 6 and a new data set 6 is thus generated.

Figure 3:
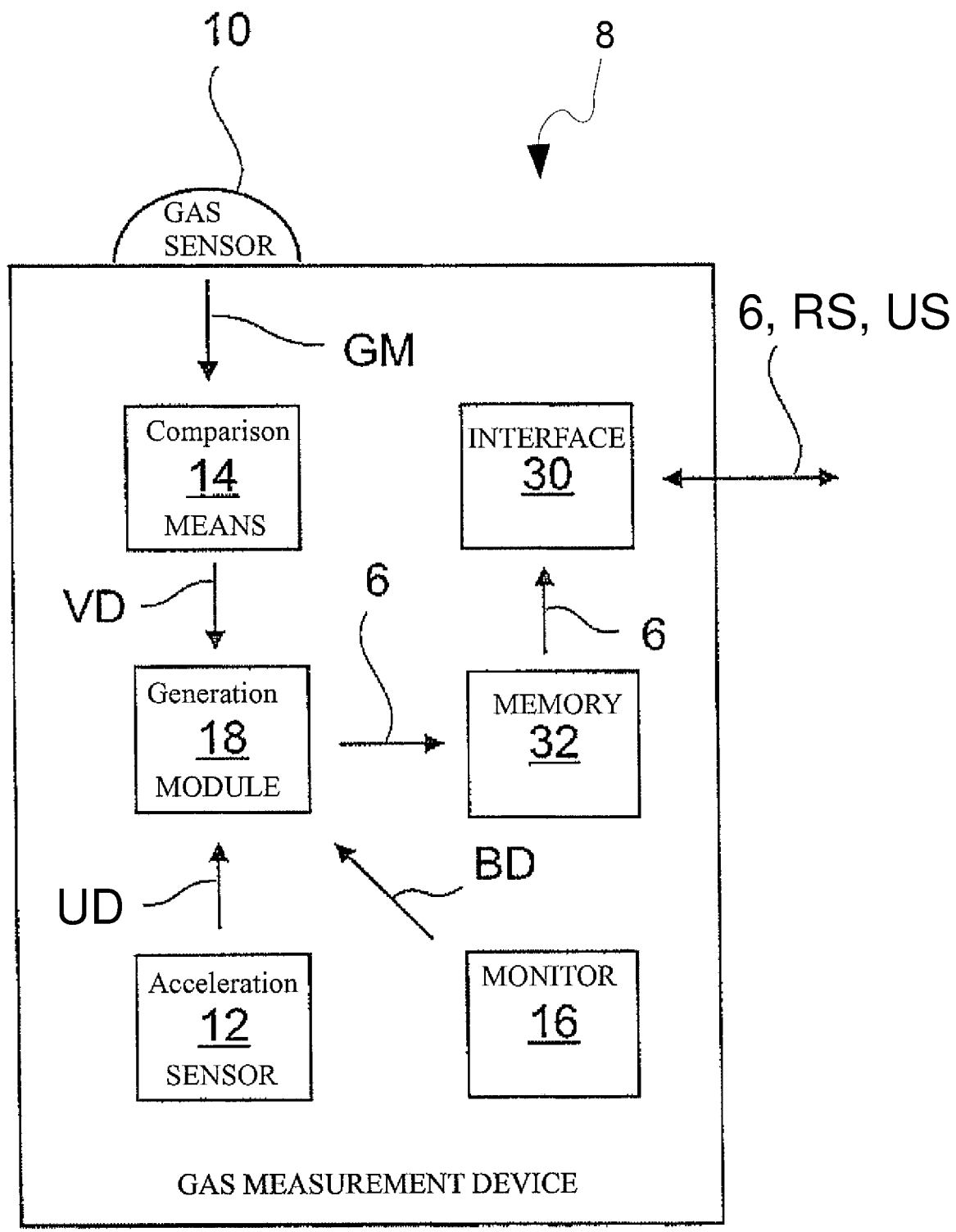
FIG. 3 is a schematic view of the design of an exemplary embodiment of a gas-measuring device according to the present invention.

Reference will now be additionally made to FIG. 3.

The gas-measuring device 8 has, besides the gas sensor 10 for detecting at least one gaseous substance, an acceleration sensor 12, a comparison means 14, a monitoring means 16, a data set generation module 18, and a gas-measuring device interface 30 in this exemplary embodiment. The comparison means 14, the monitoring means 16, the data set generation module 18, and the gas-measuring device interface 30 may be designed as pure hardware components, as pure software components, or as a combination thereof.

Accelerations acting on the gas-measuring device 8 can be detected with the acceleration sensor 12. These are in the form of acceleration data BD and are transmitted to the data set generation module 18.

The comparison means 14 is designed to compare a measured value detected with the gas sensor 10 of the gas-measuring device 8 in the form of gas concentration measured data GM with a gas concentration limit value, e.g., a workplace limit value (WLV) or with a lower explosion limit (LEL). The gas-measuring device 8 has two limit values for each gaseous substance in this exemplary embodiment, and an alarm is triggered when these limit values are exceeded. These are a low limit value, whose exceeding triggers a pre-alarm (also called A1), and a high limit value, whose exceeding triggers a master alarm (also called A2).

The current measured value of the gas sensor 10 is read out during the operation continuously or at fixed intervals and compared with the gas concentration limit value. When the gas concentration limit value is exceeded, the comparison means 14 generates comparison data VD, which are likewise transmitted to the data set generation module 18.

By contrast, the monitoring means 16 is designed to check whether a prescribed checking of the operability was performed, e.g., by performing a calibration and/or a bump test of the gas-measuring device 8, within a checking interval. The monitoring means 16 cooperates with one of the docking stations 201, 202, which generate a checking confirmation signal US after a bump test or a calibration has been performed and transmit it to the monitoring means 16 of the gas-measuring device 8 after a bump test or a calibration has been performed. The monitoring means 16 will then monitor whether one of the calibrations or bump tests was performed within the checking interval intended herefor. If the monitoring means 16 detects a skipped checking, i.e., a bump test or calibration not performed within the prescribed interval, this is available in the form of monitoring data UD, which are transmitted to the data set generation module 18.

The data set generation module 18 generates a data set 8, which is written from the data set generation module 18 into the memory 32 of the gas-measuring device 8, from the acceleration data BD, the monitoring data UD and the comparison data VD. The data set 8 being archived in the memory 32 can be read out, as was already described, via the interface 30 directly from a docking station 201, 202 and indirectly, i.e., with intermediate storage in one of the data banks 41, 42 of the docking stations 201, 202, from the central unit 200.

The mode of operation of the gas concentration monitoring system 2 will now be explained on the basis of FIGS. 1 through 3.

Before it is put into operation, a gas-measuring device 8 is usually in one of the mounting sites 501, 502, 503, 504, 505 of one of the docking stations 201, 202. The docking station 201, 202 has performed the necessary bump test or the necessary calibration of the gas-measuring device 8 and then generated a reset signal RS and transmitted same via the interface 30 of the gas-measuring device 8 to said gas-measuring device 8, which will then trigger a deletion operation of the memory 32 of the gas-measuring device 8, so that a new data set 8 is generated after the gas-measuring device 8 is put into operation.

The gas-measuring device 8 is put into operation with the removal of the gas-measuring device 8 from the mounting site 501, 502, 503, 504, 505. The monitoring means 16 is now activated and it checks whether a prescribed checking for operability was performed within the checking interval by the performance of a calibration or of a bump test.

If, furthermore, the gas-measuring device 8 was activated such that it detects gas concentrations with the gas sensor 10, the comparison means 14 is also activated at the same time and it compares the defected measured value in the form of gas concentration measured data GM with the preset gas concentration limit value.

If the monitoring means 16 now determines that a prescribed check of operability by performing a bump test or a calibration was not performed, or if the comparison means 14 determines that the preset gas concentration limit value was exceeded, the data set generation module 18 generates a data set 8 by analyzing the acceleration data BD, the monitoring data UD and/or the comparison data VD and stores this in the memory 32. Besides the information that a prescribed checking of the gas-measuring device 8 for operability was not performed, or that a gas concentration limit value was exceeded, the data set 6 may contain a gas-measuring device identification number of the gas-measuring device 8, a model number of the gas-measuring device 8, gas concentration measured data detected with the gas sensor 10 within a use interval of the gas-measuring device 8, the operating time or use interval duration of the gas-measuring device 8, acceleration values detected with an acceleration sensor 12 within a use interval of the gas-measuring device 8, or a user identification number for identifying a user.

The gas-measuring device 8 is then again placed into one of the mounting sites of the docking stations 201, 202 and the use interval is thus ended.

The data set 6 is now read out via the gas-measuring device interface 30 of the gas-measuring device 8 and stored by the data bank module of the docking station 302 in the assigned data bank 42. The data set 6 may be analyzed, e.g., directly at the docking station 202 to determine the safety code SK. However, provisions are made in this exemplary embodiment for the data set 6 to be read out by the computer 34 of the central unit 200 via a computer network, and to be archived in the data bank 40 of the central unit 200 via the input interface 22 and the data bank module 24.

It is apparent that a plurality of data sets 6, which were obtained with a plurality of gas-measuring devices 8 during a plurality of use intervals, are archived in the data bank 40.

The majority of the data sets 6 being stored in the data bank 40 of the central unit 200 can be analyzed in a further step to determine the safety code SK.

The determination of the safety code SK is carried out by the analysis module 26 of the central unit 200. The analysis module 26 performs for this a weighted addition:
of the number of skipped calibrations;
of the number of skipped bump tests; and
of the duration of the detected exceeding of the gas concentration limit value within the use interval.

The duration of the detected exceeding of the gas concentration limit value within the use interval of the gas-measuring device is the average duration of the alarm in this exemplary embodiment, i.e., the duration of a pre-alarm (A1) or of a master alarm (A2) of a plurality of gas-measuring devices 8 of a fleet of gas-measuring devices per gas-measuring device in minutes, i.e., the total duration of the alarm of all gas-measuring devices of a fleet of gas-measuring devices, divided by the number of gas-measuring devices and standardized for the number of minutes of alarm per day.

The analysis module 26 uses three different weighting factors for the weighted addition. A first weighting factor is assigned to the number of skipped calibrations, a second weighting factor is assigned to the number of skipped bump tests, and a third weighting factor is assigned to the duration of the detected exceeding of the gas concentration limit value.

The second weighting factor may be 1.5 to 3 times greater than the first weighting factor. The second weighting factor is twice the first weighting factor in this exemplary embodiment to have skipped bump tests be reflected especially heavily in the safety code.

The third weighting factor may be, by contrast, 2 to 5 times the first weighting factor. The third weighting factor is 3 times the first weighting factor and 1.5 times the second weighting factor in this exemplary embodiment, so that especially critical limit value exceedings affect the safety code especially strongly.

The analysis module 26 generates as a result a safety code SK, which contains information on how often limit values are exceeded and/or how conscientiously the gas-measuring devices 8 were checked on the basis of the information contained in the data set 8 on the limit value exceeding and/or the skipped checks of the gas-measuring devices. An intuitively easy-to-understand safety code, in which the number zero is a very good value and the scale of the safety code is open upwardly, i.e., it can assume any desired high value, is obtained by the weighted addition. It is thus not suggested, unlike in the case of data expressed in percentage, which may have a value ranging from zero to 100%, that there is a 100% risk. The safety code SK determined can in turn be archived in the data bank 40 of the central unit 200 and later compared with further safety codes SK determined later. Changes in the safety situation can thus be recognized in a simple manner.

Special safety codes SSK, which yield further, informative information concerning the model of the gas-measuring devices 8 used, the field of use of the gas-measuring devices 8, the users of the gas-measuring devices 8, the user groups of the gas-measuring devices 8 and the use time of the gas-measuring device 8, can be generated by means of the filter function 28.

The data sets 6 archived in the data bank 40 are filtered for this by means of the filter function 28 in a first analysis step before determining the respective special safety code SSK. The filter function 28 is freely programmable, so that filtering of the data sets 6 with respect to the model of the device, the field of use of the gas-measuring devices 8, the users of the gas-measuring devices 8, user groups of the gas-measuring devices 8 or the use time of the gas-measuring devices 8 is possible.

A special safety code SSK, which contains information on the reliability of individual models of the fleet of devices, on the effect of the field of use of the gas-measuring devices 8 on reliability, on problems with handling the gas-measuring devices by individual users or user groups or the effect of the use time on the reliability of the gas-measuring devices 8, is subsequently determined from the filtered data sets 6 in a second analysis step. These special safety codes SSK can also be archived in the data bank 40 of the central means 200 and compared over a longer time period with further special safety codes SSK determined later in order to make it possible to recognize changes in the safety situation in a simple manner.

Further, the safety code SK and also the special safety codes SSK can be transmitted via the computer network to the docking stations 301, 302 and displayed there with the display means 38 to inform users on the safety situation when a gas-measuring device 8 is put into operation.

While specific embodiments of the invention have been shown and described in detail to illustrate the application of the principles of the invention, it will be understood that the invention may be embodied otherwise without departing from such principles.

What is claimed is:

1. A method for determining the safety of persons with respect to at least one hazardous gas, toxic gas, combustible gas, oxygen deficiency, and oxygen excess, said method comprising the steps of:
   providing a plurality of gas measuring devices, each of said gas measuring devices comprising at least one gas sensor measuring at least one gas concentration;
   providing a memory and analysis device comprising at least one interface for receiving data from the gas measuring devices;
   transferring data from the gas-measuring devices into the memory and analysis device;
   inputting as data the concentration of each gas determined by the gas-measuring devices, as measured concentration values for the concentration into the memory and analysis device;
   determining a value rating number, for a preset period of use, of each of the gas-measuring devices in the memory and analysis device, which is an average value of the measured concentration values for the concentration of each gas;
   inputting as data a number of instances, of the measured concentration values exceeding a preset gas concentration limit value for each of the gas-measuring devices, into the memory and analysis device;
   the memory and analysis device determining a safety code by processing at least some of the received data from the gas-measuring devices, for rating the safety situation/safety of persons for a plurality of measurement sites as a whole, at which the measurements performed by the gas-measuring devices were carried out;
   determining the safety code from at least one of:
   the measured concentration values, of the plurality of gas-measuring devices;
   the value rating numbers of the plurality of gas-measuring devices; and
   a total number of instances in which a gas concentration limit value was exceeded, by the measured concentration values of the plurality of gas-measuring devices; and
   a number related to skipped calibration tests of the plurality of gas-measuring devices; and
   a number related to skipped bump tests of the plurality of gas-measuring devices; and an average of duration, the duration indicating a period the measured gas concentration exceeding a gas concentration limit value during a period of use of the respective gas-measuring device for each of the gas-measuring devices;
   providing an output device to output the safety code indicating the safety of the persons and workplace area, in which the persons using the gas-measuring devices are working.

2. A method in accordance with claim 1, wherein the step of determining the safety code further comprises:
   determining a number of checks performed on each of the gas-measuring devices during a checking interval, the checks including calibrations and/or bump tests;
   comparing the number of checks determined in the checking interval with a desired number of checks value for the checking interval; and
   taking into account a difference between the number of checks determined and the desired number of checks value in the determination of the safety code.

3. A method in accordance with claim 2, wherein the step of taking into account the difference comprises the differently weighted addition of a number of skipped calibrations and bump tests.

4. A method in accordance with claim 3, wherein the step of determining the safety code includes the weighting of a number of skipped calibrations with a first weighting factor, the weighting of a number of skipped bump tests with a second weighting factor, and the weighting of an average duration of the detected exceeding of the gas concentration limit value with a third weighting factor, wherein the safety code is the addition of the three summands each weighted with the associated weighting factor.

5. A method in accordance with claim 1, wherein the determination of the safety code is carried out by weighted addition, weighting a first summand related to the measured concentration values of the plurality of gas-measuring devices with a first weighting factor and/or weighting a second summand related to the value rating numbers of the plurality of gas-measuring devices with a second weighting factor and/or weighting a third summand related to the total number of instances in which a gas concentration limit value was exceeded by the measured concentration values of the plurality of gas-measuring devices with a third weighting factor.

6. A method in accordance with claim 1, further comprising the steps of:
   inputting as data a duration of the measured gas concentration exceeding the gas concentration limit value during a period of use of the respective gas-measuring device for each of the gas-measuring devices into the memory and analysis device, wherein the determination of the safety code is carried out such that an average duration of the received durations of the plurality of gas-measuring devices is taken into account as one weighted summand of a weighted addition.

7. A method in accordance with claim 1, further comprising the step of:

filtering data with respect to at least one of: model of the gas-measuring device and field of use of the gas-measuring device and users of the gas-measuring device and user groups of the gas-measuring device and use time of the gas-measuring device before the step of determining the safety code.

8. A method in accordance with claim 1, further comprising the step of: generating a reset signal (RS), upon receipt of which the gas-measuring device generates new data after transmission of existing data.

9. A method in accordance with claim 1, wherein the data received by the memory and analysis device from the gas-measuring devices contain at least one of:
   an identification number of the gas-measuring device; and
   a model number of the gas-measuring device; and
   gas concentration measured data detected with a gas sensor within a use interval of the gas-measuring device; and
   an operating time use interval duration, of the gas-measuring device; and
   acceleration values detected with an acceleration sensor within a use interval of the gas-measuring device; and
   a user identification for identifying a user of the gas-measuring device.

10. A memory and analysis device for a gas concentration monitoring system, the memory and analysis device comprising:
   at least one input interface for inputting data transmitted from a plurality of gas-measuring devices, said data including information regarding an average duration of gas concentrations exceeding a gas concentration limit value, a number of skipped calibration tests and a number of skipped bump tests;
   at least one data bank for storing the data and/or a data bank module for storing and reading out the data; and
   an analysis module of a central unit for analyzing the data being stored in the data bank and/or the data bank module, and for determining a safety code for rating a safety situation in a predetermined operating area by processing at least a part of the data being stored in the data bank and/or the data bank module and taking into account the average duration of gas concentrations exceeding of a gas concentration limit value, the number of skipped calibrations and the number of skipped bump tests in the determination of the safety code, the analysis module is designed to weight the number of skipped calibrations with a first weighting number, to weight a number of skipped bump tests with a second weighting number, and to weight the average duration of gas concentrations exceeding of a gas concentration limit value with a third weighting factor.

11. A memory and analysis device in accordance with claim 10, wherein the analysis module is designed to determine the number of checks performed on each gas-measuring device in a checking interval based on the received data from the gas-measurement devices, the checks including the gas calibrations and/or bump tests, to compare the number of checks performed in a checking interval with a desired value for the number of checks in a checking interval, and taking into account a difference between the checks performed and the desired value in the determination of the safety code.

12. A memory and analysis device in accordance with claim 10, wherein the analysis module has a filter function, with which the data are filtered with respect to a model of the gas-measuring devices and/or to a field of use of the gas-measuring devices and/or to users of the gas-measuring devices and/or to a user groups of the gas-measuring devices and/or to a use time of the gas-measuring devices before the determination of the safety code.

13. A memory and analysis device in accordance with claim 10, wherein the memory and analysis device is designed to generate a reset signal, upon receipt of which a gas-measuring device generates new data.

14. A memory and analysis device in accordance with claim 10, wherein the data received from a gas-measurement device contains at least one of:
   an identification number of the gas-measuring device; and
   a model number of the gas-measuring device; and
   gas concentration measured data detected with the at least one gas sensor within a use interval of the gas-measuring device; and
   an operating time use interval duration, of the gas-measuring device; and
   acceleration values detected with an acceleration sensor within a use interval of the gas-measuring device; and
   a user identification number for identifying a user of the gas-measuring device.

15. A memory and analysis device in accordance with claim 10, wherein the memory and analysis device comprises at least a docking unit for checking the operability of at least one gas-measuring device at once, the docking unit is designed to carry out calibrations and/or bump tests.

16. A memory and analysis device according to claim 10, comprising a central unit, wherein the central unit comprises a computer program product, which can be loaded into a computer of the central unit to execute, when the computer program product is being executed in the computer, method steps comprising the steps of:
   inputting a concentration of each gas determined, as measured concentration values for the concentration, by a plurality of gas-measuring devices directly into an interface of the central unit and/or into at least one interface of an docking unit of an auxiliary central unit of the memory and analysis device during a calibration or bump test performed by the docking unit on gas-measurement devices;
   determining a measured value rating number, for a preset period of use, of each of the gas-measuring devices in an analyzing module of the central unit which is an average value of the measured concentration values for the concentration of each;
   inputting a number of instances, of the measured concentration values exceeding of a preset gas concentration limit value for each of the gas-measuring devices, into the memory and analysis device; and
   determining a safety code by means of an analysis module of the central unit, for rating the safety situation/safety of persons for a plurality of measurement sites as a whole, at which the measurements performed by the gas-measuring devices were carried out, from at least one of:
   the measured concentration values, of the plurality of gas-measuring devices, and;
   the value rating numbers of the plurality of gas-measuring devices; and
   a total number of instances in which a gas concentration limit value was exceeded, by the measured concentration values, for the concentration, of the plurality of gas-measuring devices; and
   a number related to skipped calibration tests of the plurality of gas-measurement devices; and
   a number related to skipped bump tests of the plurality of gas-measurement devices; and an average of durations, each duration indicating a period the measured gas concentration exceeding a gas concentration limit value during a period of use of the gas-measurement device for each of the gas-measurement devices.

17. A gas-measuring device comprising:
at least one gas sensor for measuring a gas concentration of at least one gaseous substance to provide gas concentration measured data;
a comparison means for comparing the gas concentration measured data detected with the gas sensor with a gas concentration limit value;
a monitoring means for detecting whether prescribed operability checks, including calibrations and/or bump tests, of the gas-measuring device were performed within a checking interval;
a data set generation module for generating data, which are at least generated when the measured gas concentration measured data exceed the gas concentration limit value; and
a gas-measuring device interface for transmitting the data to a memory and analysis device;
wherein the gas-measuring device is designed to generate new data upon receiving a reset signal.

18. A gas-measuring device in accordance with claim 17, further comprising an acceleration sensor for detecting accelerations acting on the gas-measuring device.

19. A gas-measuring device in accordance with claim 17, wherein the data set generation module is designed to generate data that contains at least one of:
an identification number of the gas-measuring device; and model number of the gas-measuring device; and
gas concentration measured data detected with the gas sensor within a use interval of the gas-measuring device; and
an operating time, especially use interval duration, of the gas-measuring device; and
acceleration values detected with an acceleration sensor within a use interval of the gas-measuring device; and
a user identification number for identifying a user of the gas-measuring device.

20. A gas-measuring device with a gas sensor for measuring the gas concentration of at least one gaseous substance, also having:
a comparison means for comparing the gas concentration measured data detected with the gas sensor with a gas concentration limit value;
a monitoring means for detecting whether prescribed operability checks, including calibrations and/or bump tests, of the gas-measuring device were performed within a checking interval, and for comparison with a desired value for the number of checks performed and for generating a difference between the number of checks performed and the desired value;
a data set generation module for generating data, which are generated when the measured gas concentration measured data exceed the gas concentration limit value, and/or when the desired value for the number of checks is greater than the number of checks performed; and
a memory and analysis unit for analyzing the data to determine a safety code for rating a safety situation in a predetermined operating area by analyzing the data.

21. A gas-measuring device in accordance with claim 20, wherein the memory and analysis unit is designed to determine a number of checks performed on the gas-measuring device in a checking interval based on data received from the gas-measurement device, including calibrations and/or bump tests, for comparing the number of checks performed in a checking interval with a desired value for checks in the checking interval for a plurality of the gas-measurement devices, and/or for taking into account the difference between the number of checks performed and the desired value for checks in the checking interval for the plurality of gas-measurement devices in the determination of the safety code.

22. A gas-measuring device in accordance with claim 21, wherein memory and analysis unit is designed to take into account the skipped calibrations and bump tests of the plurality of gas-measurement devices in the determination of the safety code.

23. A gas-measuring device in accordance with claim 22, wherein the memory and analysis unit is designed to weight the number of skipped calibrations with a first weighting factor, the skipped bump tests with a second weighting factor, and/or an average duration of the detected exceeding of the gas concentration limit value with a third weighting factor.

24. A gas measuring arrangement comprising:
a plurality of mounting sites configured to perform one of a calibration test and a bump test;
a central unit connected to said mounting sites;
a plurality of portable gas measuring devices, each of said plurality of portable gas measuring device as being portable relative to each other and said central unit, said each gas measuring device including a gas sensor measuring a gas concentration in a local environment surrounding a respective said gas measuring device, said each gas measuring device storing measured values of the gas concentration, said each gas measuring device being configured to be selectively docked in one of said plurality of mounting sites and configured to be selectively removable from a respective said mounting site, said each gas measuring device being configured to be movable around a predetermined operating area relative to said central unit and other said gas measuring devices;
said each gas measuring device cooperating with a respective one of said mounting sites to perform the one test, said each gas measuring device having a desired interval between the one test, said each gas measuring device recording test data indicating performance or nonperformance of the one test at one of the desired intervals;
said central unit receiving the stored measured values and the test results for each of said gas measuring devices when the gas measuring devices are arranged in said mounting sites, said central unit generating a safety code based on the stored measured values, and performance or nonperformance of the one test, from all of the plurality of gas measuring devices;
an output device connected to said central unit, said output device receiving and displaying the safety code and informing an operator of the safety situation in the predetermined operating area.

25. An arrangement in accordance with claim 24, wherein:
said mounting sites perform both the calibration test and the bump test;
said each gas measuring device cooperating with said respective mounting site to perform both tests, said each gas measuring device having a separate desired interval between the both tests, said each gas measuring device recording test data indicating performance or nonperformance of the both tests at the desired intervals;

said central unit determines the safety code from a weighted addition of the measured values of the gas concentration and a number of non-performed bump tests and calibration tests of all said gas measuring devices.

26. An arrangement in accordance with claim 25, wherein:

said central unit determines the safety code as a numerical value with a range from zero at one end of the range with the other end being upwardly opened, the numerical value of zero for the safety code indicating a safe value and higher numbers being less safe.

27. An arrangement in accordance with claim 24, wherein:

the stored measured values include information regarding a duration of gas concentrations exceeding a gas concentration limit value, said central unit also determines the safety code from the duration of gas concentrations exceeding a gas concentration limit value.

28. A gas concentration monitoring system comprising: a memory and analysis device and a plurality of gas measurement devices, the memory and analysis device comprising:

at least one input interface for inputting data transmitted from the plurality of gas-measuring devices, at least one data bank for storing the data;

a data bank module for storing and reading out the data; and an analysis module for analyzing the data being stored to determine a safety code for rating a safety situation in a predetermined operating area by analyzing at least a part of the data being stored; and each of the gas-measuring devices of the plurality of gas-measurement devices comprising:

at least one gas sensor for measuring a gas concentration of at least one gaseous substance to provide gas concentration measured data;

a comparison means for comparing the gas concentration measured data detected with the at least one gas sensor with a gas concentration limit value;

a monitoring means for detecting whether prescribed operability checks, including calibrations and/or bump tests, of the gas-measuring device were performed within a checking interval;

a data set generation module for generating data, at least some data are generated when the measured gas concentration measured data exceed the gas concentration limit value; and at least one of a gas-measuring device interface for transmitting the data into the memory and analysis device.

29. A gas-measuring device comprising:

at least one gas sensor for measuring a gas concentration of at least one gaseous substance to provide gas concentration measured data;

a comparison means for comparing the gas concentration measured data detected with the gas sensor with a gas concentration limit value;

a monitoring means for detecting whether prescribed operability checks, including calibrations and/or bump tests, of the gas-measuring device were performed within a checking interval, the monitoring means generating monitoring data concerning whether the operability checks were performed with the checking interval;

a data set generation module for generating data, which are at least generated when the measured gas concentration measured data exceed the gas concentration limit value; and a gas-measuring device interface for transmitting the measured data and the monitoring data to a memory and analysis device, the interface being configured to make electrical contact with the memory and analysis device, the measured data and the monitoring data being readable by a computer.

\* \* \* \* \*